United States Patent [19]

Hoffer

[11] 4,124,757
[45] Nov. 7, 1978

[54] PROCESS FOR PREPARING 2,2'-ANHYDRO-1β-D-ARABINOFURANOSYL-5-FLUOROCYTOSINE AND SALTS

[75] Inventor: Max Hoffer, Nutley, N.J.

[73] Assignee: Hoffmann-La Roche Inc., Nutley, N.J.

[21] Appl. No.: 322,837

[22] Filed: Jan. 11, 1973

[51] Int. Cl.$^2$ .............................................. C07H 19/08
[52] U.S. Cl. ......................................... 536/23; 536/22
[58] Field of Search .................... 260/211.5 R; 536/23

[56] References Cited

U.S. PATENT DOCUMENTS 3,155,646  11/1964  Hunter .......................... 260/211.5 R
3,812,098  5/1974  Moffatt et al. ................ 260/211.5 R

FOREIGN PATENT DOCUMENTS 2,310,302  9/1973  Fed. Rep. of Germany .... 260/211.5 R Primary Examiner—Johnnie R. Brown
Attorney, Agent, or Firm—Samuel L. Welt; Jon S. Saxe; George M. Gould

[57] ABSTRACT 2,2'-Anhydro-1β-D-arabinofuranosyl-5-fluorocytosine (hereafter AAFC) and its acid addition salts are known compounds. AAFC may now be conveniently prepared in extremely high yield by selective acid catalyzed hydrolysis of the corresponding 3'-O-acyl analogs of AAFC which unexpectedly hydrolyzes at the acyl group while the 2,2'-anhydro linkage remains intact.

4 Claims, No Drawings

PROCESS FOR PREPARING 2,2'-ANHYDRO-1β-D-ARABINOFURANOSYL-5-FLUOROCYTOSINE AND SALTS

BACKGROUND OF THE INVENTION

AAFC has recently been prepared and its valuable medicinal activity is described in a paper by Fox et al., Cancer Research 32, 2269 (1972). The method of preparation involves a modification of the Kikugawa et al. procedure which was described in J. Org. Chem. 37, 284 (1972). This modified procedure involves reaction of a Vilsmeier-Haak reagent with 5-fluorocytidine followed by isolation of the formate salt of AAFC by ion exchange techniques.

The 3'-O-acyl derivatives of AAFC have been described in West German Pat. No. 2,113,724 (claiming priority from U.S. patent application Ser. No. 21,206, filed March 19, 1970, now U.S. Pat. No. 3,812,098).

SUMMARY OF THE INVENTION

Acid hydrolysis of the readily available 3'-acyl derivatives of AAFC produces AAFC and its acid addition salts in high purity and in nearly quantitative yields. The selective attack on the 3'-acyl bond with concomitant stability of the 2,2'-anhydro linkage under the hydrolysis conditions can be regarded as surprising in view of the indications by Kikugawa et al., supra, at page 286 that the related compound 2,2'-anhydroarabinosylcytosine is quantitatively cleaved to arabinosylcytosine in aqueous solution in 15 minutes at room temperature. Moreover, at page 287 of that article the same compound was shown to be labile in an acidic aqueous solution.

However, Doerr and Fox, J. Org. Chem., 32, 1462 (1967) do indicate on page 1468 that the anhydro-linkage in 2,2'-anhydroarabinosylcytosine is stable in water or acid although unstable in solutions of increased hydroxyl ion concentration. It is further indicated that the aforesaid compound in free form is a relatively strong base which in water is autohydrolyzed to arabinosylcytosine.

DESCRIPTION OF THE INVENTION

The present invention relates to an improved process for the preparation of AAFC and its acid addition salts by selective acid hydrolysis of the readily available 3'-O-acyl analogs or acid addition salts thereof.

Suitable acyl substituents useful in the starting materials for the process of this invention include organic radicals such as $C_{1-8}$ alkanoyl, for example, acetyl, butyryl, hexanoyl and the like; monocyclic aroyl, for example, benzoyl; $C_1$-$C_3$ alkyl monocyclic aroyl, for example, toluoyl; $C_{4-8}$ cycloalkanoyl, for example cyclopentanoyl and saturated or unsaturated heterocyclic hydrocarbonoyl groups containing sulfur, nitrogen or oxygen hetero atoms such as thionyl, pyrroloyl, furoyl, pyrazoloyl, furazanoyl, isothiazoloyl, indolyl and the like. A particular preferred acyl group is acetyl.

The acidic medium utilized in the selective hydrolysis will have a pH below about 3, most preferably below about 0. The medium may be aqueous or may comprise a $C_1$-$C_4$ lower alkanol such as preferably methanol or mixtures thereof.

Useful acids in the present process include inorganic acids, such as for example, mineral acids like HCl, HBr, $H_2SO_4$, $HNO_3$, or $H_3PO_4$ or sulfonic acids such as p-toluenesulfonic acid or methanesulfonic acid may also be utilized successfully. Preferred embodiments of this invention employ mineral acids, most preferably HCl, in a lower alkanol, most preferably methanol. In this manner AAFC is obtained in crystalline form in high yield directly from the reaction medium as the hydrochloride salt.

The reaction temperatures employed is not narrowly critical. Generally a temperature in the range of from about 20° C. to the reflux temperature of the reaction mixture may be utilized. Most preferably the reaction is conducted at the reflux temperature of the reaction medium. The fact that the 2,2'-anhydro linkage will remain intact under these vigorous conditions must be considered surprising.

It is evident that selection of the acid employed in the hydrolysis can determine the nature of the acid addition salt of AAFC produced. Thus, for example, use of hydrochloric acid in the reaction will produce AAFC as its hydrochloride acid addition salt which crystalizes directly from the reaction mixture. If other addition salts are desired modification can be made by either selecting another acid for the hydrolysis or alternatively subjecting the hydrolysis produced to ion exchange procedures well known in the art. In such manner AAFC can be prepared as the following acid addition salts: formate, hydrochloride, hydrobromide, sulfate, phosphate, acetate, oxalate, succinate, maleate, benzoate and the like. Non-pharmaceutically acceptable acid addition salts of AAFC produced herein may be converted to pharmaceutically acceptable acid addition salts by procedures well known in the art such as by treatment with ion-exchange resins.

EXAMPLE 1

20 g. of 3'-acetyl-2,2'-anhydro-1-beta-D-arabinofuranosyl-5-fluorocytosine hydrochloride, crude, were refluxed with 80 ml. of 3 n aqueous hydrochloric acid under vigorous stirring for 20–30 minutes. The product crystallized from the reaction medium even at the elevated temperature. After addition of 25o ml. 2-propanol and refrigeration the product was filtered by suction. Yield 17 g. (98.5%) of 2,2'-anhydro-1-beta-D-arabinofuranosyl-5-fluorocytosine hydrochloride. M.P. 184° (dec.) U.V. max. 238 and 280 nm $[\alpha]_D^{25}$ = 43.39.

EXAMPLE 2

33 g. of 3'-acetyl-2,2'-anhydro-1-beta-D-arabinofuranosyl-5-fluorocytosine hydrochloride were refluxed with 600 ml. methanol and 20 ml. methanolic HCl (saturated at 25°) for 45 minutes. After cooling the product was filtered by suction, yielding 24.4 g. of pure 2,2'-anhydro-1-beta-D-arabinofuranosyl-5-fluorocytosine hydrochloride. A second crop of 3.6 g. was obtained upon evaporation of the filtrate. Combined yield: 98%.

EXAMPLE 3

The starting material for Examples 1 and 2 may be prepared as follows: In a 1 L three neck round bottom flask equipped with heating mantle, mechanical stirrer and reflux condenser there were suspended 26 g.. fluorocytidine, in a mixture of 20 ml. DMFA and 200 ml. acetonitrile, and the mixture heated to beginning of reflux. 30 g. of acetyl methyl-lactic acid chloride, J.A.C.S. 68, p. 331 (1946) were added. The solid went rapidly in solution and soon the product began to crystallize in voluminous white needles. Refluxing under stirring was continued for 30 minutes when the vessel was filled with a thick crystallization of the product. After allowing to cool it was slurried with 500–1000 ml. of acetone and filtered through a hardened filter by suction. Yield 32 g. (97%) of 3'-acetyl-2,2'-anhydro-1-beta-D-arabinofuranosyl-5-fluorocytosine hydrochloride, m.p. 270–273°.

I claim:

1. In a process for the preparation of 2,2'-anhydro-1-beta-D-arabinofuranosyl-5-fluorocytosine and its acid addition salts by the selective hydrolysis of 3'-O-acyl-2,2'-anhydro-1-beta-D-arabinofuranosyl-5-fluorocytosine or an acid addition salt thereof, the improvement which comprises conducting said acid hydrolysis in an acid medium comprising a mineral acid in aqueous or a $C_{1-14}$ alkanol medium at a pH below about 0 at the reflux temperature of the reaction mixture for up to about 45 minutes so as to selectively hydrolyze the acyl group at the oxygen atom on the 3'-position starting compound and whereby said product 2,2'-anhydro-1-beta-D-arabinofuranosyl-5-fluorocytosine and its acid addition salts is crystallized directly from said reaction medium.

2. The process of claim 1 wherein said acid medium comprises methanolic hydrogen chloride.

3. The process of claim 1 wherein said acid medium comprises aqueous hydrogen chloride.

4. The process of claim 1 wherein said 3'-O-acyl substituent on the starting material is 3-O-acetyl.

* * * * *